US012569448B2

(12) United States Patent
Hermann et al.

(10) Patent No.: US 12,569,448 B2
(45) Date of Patent: Mar. 10, 2026

(54) MEMBRANE-BASED TWO COMPONENT THERAPEUTIC GAS RELEASE SYSTEM FOR ORAL ADMINISTRATION

(71) Applicant: Julius-Maximilians-Universitaet Wuerzburg, Wuerzburg (DE)

(72) Inventors: Cornelius Hermann, Wuerzburg (DE); Lorenz Meinel, Wuerzburg (DE); Wolfgang Schmehl, Gruenwald (DE); Kevin Popp, Neustadt/Aisch (DE); Simon Reilaender, Wuerzburg (DE)

(73) Assignee: Julius-Maximilians-Universitaet Wuerzburg, Wuerzburg (DE)

( * ) Notice: Subject to any disclaimer, the term of this patent is extended or adjusted under 35 U.S.C. 154(b) by 880 days.

(21) Appl. No.: 17/766,722

(22) PCT Filed: Oct. 13, 2020

(86) PCT No.: PCT/EP2020/078794

§ 371 (c)(1),
(2) Date: Apr. 5, 2022

(87) PCT Pub. No.: WO2021/074159

PCT Pub. Date: Apr. 22, 2021

(65) Prior Publication Data

US 2024/0122862 A1 Apr. 18, 2024

(30) Foreign Application Priority Data

Oct. 14, 2019 (EP) .................................... 19203033

(51) Int. Cl.
*A61K 9/48* (2006.01)
*A61K 33/04* (2006.01)

(52) U.S. Cl.
CPC ............ *A61K 9/485* (2013.01); *A61K 9/4808* (2013.01); *A61K 9/4816* (2013.01); *A61K 33/04* (2013.01)

(58) Field of Classification Search
CPC .... A61K 9/485; A61K 9/4808; A61K 9/4816; A61K 33/04
See application file for complete search history.

(56) References Cited

U.S. PATENT DOCUMENTS 5,882,674 A * 3/1999 Herrmann ................. A61P 9/10
424/448

FOREIGN PATENT DOCUMENTS

| | | | | |
|---|---|---|---|---|
| EP | 3524290 | A1 | 8/2019 | |
| WO | WO-2015188941 | A1 * | 12/2015 | ........... A61K 31/555 |
| WO | WO-2016110517 | A1 * | 7/2016 | ........... A01N 1/0226 |
| WO | WO 2018/112255 | A1 | 6/2018 | |
| WO | WO-2018149826 | A1 * | 8/2018 | ................ C08J 9/08 |

OTHER PUBLICATIONS

Wolburn et al.; Overcoming safety challenges in CO therapy—Extracorporeal CO delivery under precise feedback control of systemic carboxyhemoglobin levels; Elsevier; Journal of Controlled Release 279 (2018) 336-344 (Year: 2018).*
Christoph Steiger et al., "Oral Drug Delivery of Therapeutic Gases—Carbon Monoxide Release for Gastrointestinal Disease", J. Controlled Release, vol. 189, pp. 46-53 (Jun. 24, 2014).
Christoph Steiger et al., "Localized Delivery of Carbon Monoxide", Eur. J. Pharm. and Biopharm, vol. 118, pp. 3-12 (Sep. 1, 2017).

* cited by examiner

*Primary Examiner* — Robert A Wax
*Assistant Examiner* — John W Lippert, III
(74) *Attorney, Agent, or Firm* — Smith Patent, LLC; Chalin A. Smith

(57) ABSTRACT

The present invention discloses a therapeutic gas release system for oral administration comprising a therapeutic gas releasing compound A, and a therapeutic gas release triggering compound B, wherein compound A and B are separated from each other by an inner septum during storage of the system, wherein compound A and B are surrounded by an outer membrane, which is a gas-permeable and water- and solid-impermeable membrane, preferably a silicone membrane, and wherein therapeutic gas release from the system is activated before oral administration by breaking the inner septum. The therapeutic gas released from the system of the present invention is suitable for the treatment of (inflammatory) diseases of the gastrointestinal tract.

18 Claims, 7 Drawing Sheets

MEMBRANE-BASED TWO COMPONENT THERAPEUTIC GAS RELEASE SYSTEM FOR ORAL ADMINISTRATION

PRIORITY

This application corresponds to the U.S. National phase of International Application No. PCT/EP2020/078794, filed Oct. 13, 2020, which, in turn, claims priority to European Patent Application No. 19203033.6 filed Oct. 14, 2019, the contents of which are incorporated by reference herein in their entirety.

TECHNICAL FIELD OF THE PRESENT INVENTION

The present invention relates to therapeutic gas releasing systems for oral administration.

BACKGROUND OF THE PRESENT INVENTION

Gases such as carbon monoxide (CO), nitric oxide (NO) and/or hydrogen sulfide ($H_2S$), which have been traditionally considered as harmful gases, are a current field of research with respect to their use as therapeutic gases. CO, for example, has beneficial impacts on inflammatory conditions, e.g. in the gastrointestinal tract. Further therapeutic applications of CO, as well as of NO and $H_2S$, have e.g. been described in WO 2015/188941 A1.

Gases like oxygen and nitric oxide are already implemented in clinical practice and are administered either by inhalation ($O_2$, in certain indications also NO) or in a chemically bound form (e.g. NO as nitroglycerin). However, carbon monoxide, hydrogen sulfide and nitric oxide also have a high toxic potential, and accordingly, the administration via inhalation is limited by general handling complexity and safety issues posing medical personal and the patient at risk, e.g. in case of accidental release.

An alternative approach for the administration of therapeutic gases has been described using therapeutic gas releasing compounds that release therapeutic gases such as CO, NO and $H_2S$ by reaction with a gas release triggering compound. Therapeutic gas release systems for oral administration using this principle are for example disclosed in WO 2015/188941 A1; C. Steiger et al., "Oral drug delivery of therapeutic gases—Carbon monoxide release for gastrointestinal diseases", Journal of Controlled Release, 189 (2014), 46-53; and C. Steiger et al., "Prevention of colitis by controlled oral drug delivery of carbon monoxide", Journal of Controlled Release, 239 (2016), 128-136.

However, a problem associated with these oral therapeutic gas release systems is the formation of toxic degradation products derived from the therapeutic gas releasing molecules upon reaction with the gas triggering compound as well as the central metal ion of the compounds themselves. Studies assessing the toxicity of products derived from CORM-2 and sodium sulfite in aqueous solution with a fibroblast cell line have shown that exposure of the cells for 24 hours resulted in a significant reduction of cell survival (C. Steiger et al., Journal of controlled release, 239 (2016), 128-136).

WO 2016/110517 A1 discloses a gas delivery device, wherein the problem of toxicity derived from degradation products of the gas releasing compounds is addressed by using a gas permeable and liquid and solid impermeable membrane, e.g. a silicone membrane that prevents toxic degradation products from leaving the device. However, the gas delivery device disclosed in WO 2016/110517 is not suitable for therapeutic purposes, let alone for oral administration. Rather, this device is intended for gas delivery to extra-corporeal transplants, extra-corporeal cells, a brain-dead transplant or food stuff.

DE 10 2017 006 393 A1 discloses CO releasing systems comprising a metal carbonyl compound and a triggering compound, which are suitable for use in therapy. However, this document does not disclose how to administer the CO releasing system to a patient in order to benefit from its therapeutic potential, let alone how such systems should be designed in order to avoid that toxic degradation products are released into the body of the patient upon administration.

Thus, there is a need for therapeutic gas releasing systems for oral administration, which overcome the problem of toxicity associated with the release of toxic degradation products into the patient's body, which means that the system is also required to maintain its mechanical integrity during swallowing and transit through the gastrointestinal tract. The therapeutic system should also allow control of the total amount of therapeutic gas to be released as well as of the release rates in order to be flexible in terms of reaching different regions of the gastrointestinal tract. Moreover, therapeutic gas release should not be triggered during storage of the therapeutic system, but system should involve a mechanism that allows the patient or the physician to reliably activate therapeutic gas release shortly before oral administration of the system.

SUMMARY OF THE PRESENT INVENTION

The present invention overcomes the above mentioned problems by providing a:

1. Therapeutic gas release system for oral administration comprising:
   a therapeutic gas releasing compound A, and
   a therapeutic gas release triggering compound B,
   wherein compound A and B are separated from each other by an inner septum during storage of the system, wherein compound A and B are surrounded by an outer membrane, which is a gas-permeable and water- and solid-impermeable membrane, preferably a silicone membrane, and wherein therapeutic gas release from the system is activated before oral administration by breaking the inner septum.
2. Therapeutic gas release system according to item 1, wherein the inner septum breaks upon squeezing the system manually or in a partly automated process using an external activator device.
3. Therapeutic gas release system according to item 1 or 2, wherein compound A is in a first unit and compound B is in a second unit, and wherein the first and second unit are surrounded by the outer membrane.
4. Therapeutic gas release system according to item 3, wherein the inner septum forms part of the second unit and the first unit has one open end that points towards the inner septum; and wherein the system is configured that the first unit can be pushed towards the inner septum by squeezing the system along its longitudinal axis, causing the inner septum to break.
5. Therapeutic gas release system according to item 3 or 4, wherein the second unit comprises a top that closes an open end of the second unit, wherein the top is optionally glued to the second unit using an adhesive.

6. Therapeutic gas release system according to any of items 3 to 5, wherein the first unit, the second unit and the top of the second unit are made of a biocompatible material.
7. Therapeutic gas release system according to any of items 3 to 6, wherein the first unit is made of a thermoplastic material, which is preferably polyamide, and/or the second unit and/or the top of the second unit is/are made of a thermoset material, which is preferably an acrylic resin or an epoxy resin.
8. Therapeutic gas release system according to any of the preceding items, wherein the outer membrane is tubular, and wherein the open ends of the tubular outer membrane are closed with an adhesive, preferably a silicone adhesive.
9. Therapeutic gas release system according to any of items 3 to 8, wherein the therapeutic gas release system corresponds to the embodiment shown in FIG. 1, wherein (1) is the first unit comprising an obliquely tapered hollow tip open end (1a) with one or more elevations (1 b) pointing towards the inner septum; (2) is the second unit; (3) is a top closing the open end of the second unit; (4) is the inner septum separating compound A and compound B from each other during storage of the system, wherein the inner septum is shifted towards the center of the second unit; (5) is a tubular outer membrane surrounding the first and second unit; and (6) is an adhesive, preferably a silicone adhesive, closing the open ends of the outer membrane; wherein the system is configured that the first unit is pushed towards the inner septum by squeezing the system along its longitudinal axis, causing the inner septum to break.
10. Therapeutic gas release system according to any of the preceding items, wherein the therapeutic gas is carbon monoxide (CO), hydrogen sulfide ($H_2S$) or nitric oxide (NO), preferably carbon monoxide (CO).
11. Therapeutic gas release system according to any of the preceding items, wherein compound A is a carbon monoxide releasing molecule (CORM), a hydrogen sulfide ($H_2S$) releasing molecule or a nitric oxide (NO) releasing molecule, preferably a carbon monoxide releasing molecule, more preferably a metal carbonyl compound, even more preferably a molybdenum carbonyl compound.
12. Therapeutic gas release system according to any of the preceding items, wherein compound B is a sulfur containing compound, a nitrogen containing compound, an oxidizing compound or water.
13. Therapeutic gas release system according to preceding items, wherein the therapeutic gas is carbon monoxide (CO), the therapeutic gas releasing compound A is a molybdenum carbonyl compound, preferably $Mo(CO)_3(CNCH_2CO_2H)_3$, and the therapeutic gas release triggering compound B is $FeCl_3$, $Ce(SO_4)_2$ or $H_2O_2$, preferably $FeCl_3$.
14. Therapeutic gas release system according to any of the proceeding items for use in the treatment of diseases of the gastrointestinal tract.
15. Therapeutic gas release system according to item 14, wherein the therapeutic gas is carbon monoxide and the therapeutic gas release system is for use in the treatment of inflammatory diseases of the gastrointestinal tract, said inflammatory diseases being preferably selected from the group consisting of colitis ulcerosa, gastric ulcera, postoperative ileus, diabetic gastroparesis and Morbus Crohn.
16. Therapeutic gas release system according to any of the preceding items, wherein the system is surrounded by a protective shell.

The present invention and further preferred embodiments will be described in detail herein below.

DETAILED DESCRIPTION OF THE PREFERRED EMBODIMENTS

Figure 1:
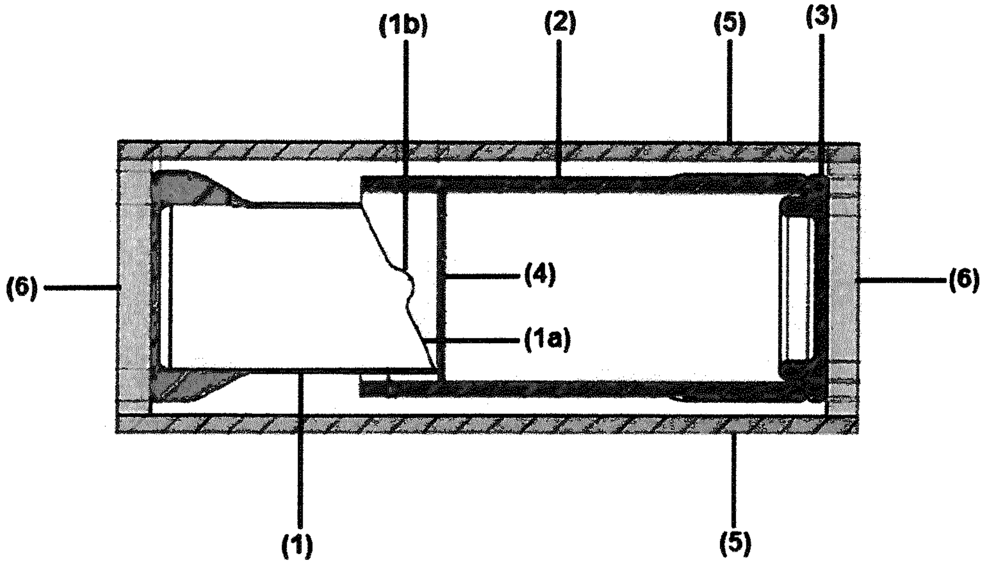
FIG. 1 is a cross-sectional view of a preferred embodiment of the present invention, wherein (1) is the first unit comprising an obliquely tapered hollow tip open end (1a) with one or more elevations (1b) towards the inner septum; (2) is the second unit; (3) is a top closing the open end of the second unit; (4) is the inner septum separating compound A and compound B from each other during storage of the system, wherein the inner septum is shifted towards the center of the second unit; (5) is a tubular outer membrane surrounding the first and second unit; and (6) is an adhesive, preferably a silicone adhesive, closing the open ends of the outer membrane; wherein the system is configured that the first unit is pushed towards the inner septum by squeezing the system along its longitudinal axis, causing the inner septum to break.

The therapeutic gas release system of the present invention allows for an efficient and safe administration of a therapeutic gas, including, but not limited to carbon monoxide (CO), hydrogen sulfide ($H_2S$) and nitric oxide (NO), wherein carbon monoxide (CO) is the preferred therapeutic gas to be delivered. If the therapeutic gas of the present invention releases CO (which is the case if a CO releasing molecule is used as compound A), the system of the present invention can also be designated as "CO release system for oral administration". Analogously, if the therapeutic gas of the present invention releases $H_2S$ or NO (which is the case if a $H_2S$ or NO releasing molecule is used as compound A), it can also be designated as "$H_2S$ release system for oral administration" and "NO release system for oral administration", respectively.

The therapeutic gas release system of the present invention can be stored without the risk that a reaction between compound A and compound B takes places before administration of the system due to the separation of compound A and compound B by the inner septum comprised in the system. The system can be activated shortly before use, i.e. before its oral administration, by means of applying force to it, wherein said force is applied by manually squeezing (compressing, pressing together) the system by the patient or physician before use. Alternatively, the force can be applied in a partly automated process by means of squeezing the system with the help of an external activator device. Squeezing the system in such manner will result in pressure on the inner septum, which, as a consequence, will break, thereby bringing compound A and B into contact, resulting in a chemical reaction between the two compounds that results in therapeutic gas release which can leave the system via the outer membrane. The system of the present invention thus comprises a mechanism that allows initiation of the chemical reaction between compound A and compound B when it is needed, i.e. shortly before its oral administration. After activation, the system of the invention can be orally administrated to the patient. The force applied to the system in order to break the inner septum before oral administration is designated herein also as "breaking force".

The outer membrane of the therapeutic gas release system of the present invention is gas-permeable, but water- and solid-impermeable. This makes the therapeutic gas release system of the present invention particularly safe for oral administration because it avoids the release of toxic degradation products and/or metal ions, which derive from the therapeutic gas releasing compound A in the course of the reaction with compound B, into the body of the patient. Suitable materials for the gas-permeable, but water- and solid-impermeable outer membrane used in the system of the present invention, without being limited to them, include polytetrafluoroethylene (PTFE) and silicone, wherein silicone is preferred.

The therapeutic gas release system of the present invention features some further advantages including that the therapeutic gas release rate can be controlled by tailoring the characteristics of the outer membrane, e.g. in terms of its wall thickness. For example, an outer membrane with a thinner wall favors a faster release of the therapeutic gas, whereas an outer membrane with a thicker wall favors a slower release of the therapeutic gas. The therapeutic gas release rate of the therapeutic gas can also be tailored by the formulation of the therapeutic gas releasing compound A in the system of the present invention. Compound A can e.g. be used in a non-compressed form, which increases the release rate. Alternatively, it can be used in a pre-compressed form, eventually further comprising a coating, which decreases the release rate. Adjusting the release rate of the therapeutic gas from the system of the present invention by means of the above measures allows for local therapy in different sections of the gastrointestinal tract, e.g. the stomach in case of a faster release, and the small intestine and colon in case of a slower release of the therapeutic gas.

Moreover, the absolute amount of therapeutic gas to be released within the gastrointestinal tract can be controlled, because the system is flexible in terms of its size and allows to freely choose the amounts of therapeutic gas releasing compound A and the therapeutic gas release triggering compound B.

In the therapeutic gas release system of the present invention, compound A and compound B are separated from each other by the inner septum during storage. This avoids that a chemical reaction between compound A and compound B takes place spontaneously. Material and strength (thickness) of the inner septum are chosen in order to avoid spontaneous and arbitrary damage during storage. Accordingly, the system of the present invention can be stored for some time before use.

On the other hand, the inner septum is designed to break upon applying force to it. As described above, said force can be applied by the patient or physician directly before the oral administration of the system by means of manually squeezing (compressing, pressing together) the system of the present invention. Squeezing the system "manually" thus means that the patient or physician can make the inner septum break without further auxiliary measures than using their hands. Alternatively, said force can also be applied by means of squeezing the system with the help of an external activator device in a partly automated process.

Typically, the inner septum has a thickness between 0.1 and 0.4 mm, preferably between 0.15 and 0.25 mm. It is typically made of an inert polymer material, which is preferably a thermoset material (duroplast). Particularly preferred are acrylic resins or epoxy resins as the material for the inner septum.

The breaking force required for breaking the inner septum in the system of the present invention is a function of the thickness of the inner septum at a given material of the inner septum. The breaking force required for breaking the inner septum is typically from 6 to 80 N in the system of the present invention. A breaking force within this range ensures that the activation of the system of the present invention before oral administration is easy to be performed manually by the patient or physician, but also that (unintended) activation of the system of the present invention during storage is avoided. The lower the breaking force is, the easier it is for the patient or physician to activate the system of the present invention before its administration. The higher the breaking force is, the more stable is the system of the present invention during storage. Preferably, the breaking force is from 7 to 65 N, more preferably from 8 to 50 N, even more preferably from 9 to 35 N, and particularly preferably from 10 to 20 N.

The breaking force required for breaking the inner septum in the system of the present invention can be determined using a standard tablet hardness tester, which complies with current USP (chapter 1217, tablet breaking force) and EP (2.9.8, resistance to crushing of tablets) requirements, such as the Dr. Schleuniger® Pharmatron 8M Tablet Hardness Tester. The breaking force required for breaking the inner septum in the system of the present invention is accordingly determined like in a conventional tablet.

The system of the present invention can thus also be described as a gas release system for oral administration comprising a therapeutic gas releasing compound A and a therapeutic gas release triggering compound B, wherein compound A and B are separated from each other by an inner septum during storage of the system, wherein compound A and B are surrounded by an outer membrane, which is a gas-permeable and water- and solid-impermeable membrane, preferably a silicone membrane, wherein the inner septum breaks at a breaking force ranging from 6 to 80 N, preferably from 7 to 65 N, more preferably from 8 to 50 N, even more preferably from 9 to 35 N, and particularly preferably from 10 to 20 N.

Ways how to apply the force required to break the inner septum have been described above.

After breaking of the inner septum, compound A and compound B come into contact, resulting in release of therapeutic gas due to a chemical reaction between compound A and compound B. The therapeutic gas release system is now activated and can be orally administered. The system of the present invention being "activated" thus means that the inner septum has broken and a chemical reaction between compound A and compound B can take place. In order to support mixing of compound A and compound B after breaking of the inner septum, the system may also be shaken for a while (preferably 5 to 20 second) before oral administration.

In order to confirm that the inner septum has broken, the patient or physician can e.g. check the system visually before oral administration. In certain preferred embodiments of the present invention, in particular embodiments wherein the system includes a first and a second unit comprising compound A and B, respectively, the patient or physician will feel a resistance upon squeezing the system, which resolves once the inner septum has broken.

After activation of the system, therapeutic gas leaves the system through the outer membrane, which is gas permeable, and liquid and solid impermeable membrane comprising, preferably consisting of silicone. Due to these characteristics of the outer membrane, toxic degradation products and the metal ions from the CORM are retained within the system and are not released into the patient's body. The outer membrane moreover confers mechanical stability to the system, which allows swallowing of the system and transport through the gastrointestinal tract typically without mechanical damage. After transit through the gastrointestinal tract, the system is naturally excreted by the patient.

The outer membrane can for example have a round or oval shape. Preferably, it has a tubular shape with two open ends that can be closed after assembly of the system by gluing them with an adhesive. The adhesive used in the present invention is an adhesive suitable for pharmaceutical applications. Preferably, it is a silicone adhesive, more preferably a UV-curing or an acetate-crosslinking silicone adhesive. An example for an adhesive that is preferably to be used in the present invention is Loctite® SI 5248.

Depending on the physical state of compound A under standard conditions (1013 hPa, 23° C.), it can be used in solid or liquid form in the system of the present invention. Alternatively, it can also be used as an aqueous solution. Preferably, compound A is used in solid form in the system of the present invention.

Compound B can also be used in solid or liquid form, depending on its physical state under standard conditions, or in solubilized form in the system of the present invention. It is preferable that compound B is used in liquid form or in aqueous solution. Using compound B in aqueous solution is particularly preferred because this increases the rate of the chemical reaction between compound A and compound B, in particular if compound A is used in solid form, which is preferable. The release rate of the therapeutic gas from the system is also controlled by the characteristics of the outer membrane, in particular the wall thickness.

In a preferred embodiment of the present invention, compound A is contained in a first unit and compound B is contained in a second unit, and the first and second unit are surrounded by the outer membrane. In this embodiment, compound A and B are still separated from each other by the inner septum during storage of the system, which breaks upon applying force to it. The inner septum can be between the first and the second unit, it can also be part of the first unit, or it can be part of the second unit.

The outer diameter of the first unit is typically smaller than the inner diameter of the second unit. Such a geometry of the first and second unit is beneficial when applying force to the system along its longitudinal axis in order to break the inner septum for activation of the system.

First and second unit have at least one opening (open end) that can be used for filling the units with compound A and compound B, respectively, before assembly of the system of the present invention. These openings can be closed with a tight-sealing top after filling the units with compound A and compound B, respectively, before assembly of the system of the present invention. The top can additionally be glued to the unit using an adhesive as described above.

In a preferred embodiment of the present invention, the inner septum forms part of either the first and the second unit, and the other unit points with an open end towards the inner septum, which allows mixing of compound A and compound B after breaking of the inner septum, resulting therapeutic gas release from the system of the present invention.

Preferably, the first unit has one open end, which points towards the inner septum that separates compound A and compound B during storage of the system and forms part of the second unit. This configuration allows that after breaking of the inner septum, compound A and compound B easily come in contact with each other, thereby activating the system of the present invention for therapeutic gas release.

In this embodiment, the first unit can be pushed towards the inner septum by means of squeezing system along its longitudinal axis, resulting in pressure on the inner septum once the first unit comes into contact with the inner septum as a result of squeezing the system. As a consequence thereof, the inner septum bends and eventually breaks, bringing compound A and B into contact.

In a further preferred embodiment, the shape of the first unit facilitates breaking of the inner septum upon squeezing the system. For example, the first unit can have an obliquely tapered hollow tip open end pointing towards the inner septum, optimally comprising one or more elevations ("noses") on the obliquely tapered hollow tip open end pointing towards the inner septum.

In a particularly preferred embodiment, the first unit has a cylindrical shape with an obliquely tapered hollow tip open end with further elevations on the obliquely tapered hollow tip open end pointing towards the inner septum. This configuration allows a particularly easy, safe and reproducible mechanism for breaking the inner septum that separates compound A in the first unit from compound B in the second unit during storage of the system is provided. The material and strength (thickness) of the inner septum are chosen in order to avoid spontaneous and arbitrary damage during storage, but to allow breaking upon squeezing the system.

The inner septum preferably forms part of the second unit, which contains compound B. The inner septum in that case closes one end of the second unit, said end pointing towards the first unit in the system of the present invention. Preferably, the second unit has a cylindrical shape. It is furthermore preferred that the inner septum is slightly shifted towards the center of the second unit. This configuration allows that the first unit and second unit can be easily pushed towards each other when the system is squeezed along its longitudinal axis, resulting in pressure on the inner septum upon contact with the first unit, causing the inner septum to bend and eventually to break. Thus, this configuration constitutes a particularly effective mechanism to activate the system of the present invention before oral administration.

FIG. 1 shows a cross-sectional view of a preferred embodiment of the present invention.

Figure 2:
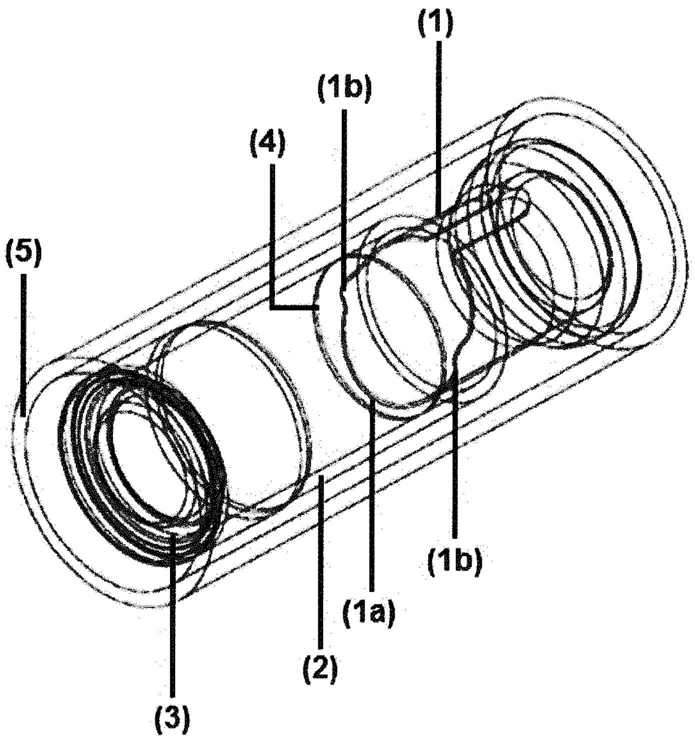
FIG. 2 is a perspective view of a preferred embodiment of the present invention, wherein (1) is a cylindrical first unit comprising an obliquely tapered hollow tip open end (1a) with two elevations (1b) pointing towards the inner septum; (2) is a cylindrical second unit; (3) is a top closing the open end of the second unit; (4) is the inner septum separating compound A and compound B from each other during storage of the system, wherein the inner septum is shifted towards the center of the second unit; (5) is a tubular outer membrane surrounding the first and second unit; wherein the system is configured that the first unit is pushed towards the inner septum by squeezing the system along its longitudinal axis, causing the inner septum to break.

FIG. 2 shows a perspective view of a preferred embodiment of the present invention, wherein first and second unit have a cylindrical shape. "Cylindrical shape" as used herein means the basic geometrical shape of the unit. It is, however, not excluded that the overall shape of the units deviates from a perfect cylinder.

The therapeutic gas release system of the present invention, wherein compound A is in a first unit and compound B is in a second unit, is typically assembled by manually filling the first unit with compound A, preferably in solid form, and manually filling the second unit with compound B, in solid, liquid or solubilized form. If necessary, openings of the first and second unit are closed with a tight-sealing top, which can additionally be glued to the unit using an adhesive, before the outer membrane is installed. This can e.g. be realized by inserting the first unit filled with compound A and the second unit filled with compound B into a tubular outer membrane. After inserting the first and second unit, the open ends of the tubular membrane are closed using an adhesive, which is preferably a silicone adhesive.

It is also possible to assemble the system of the present invention in a (partly) automated process. After manually filling the first and second unit with compound A and compound B, respectively, the units can be closed in an automated process with an adhesive, preferably a silicone adhesive, more preferably with a UV-curing silicone adhesive (e.g. Loctite® SI 5248) before curing the adhesive in a UV chamber. The units can then be inserted in an automated process into a tubular outer membrane, the open ends of which are glued with an adhesive, preferably a silicone adhesive, more preferably with a UV-curing silicone adhesive.

The first unit, the second unit and tops used for closing the first unit and/or the second unit consist of inert and biocompatible polymer materials, which can e.g. be produced by 3D printing (e.g. selective laser sintering or poly-jet modelling) or by microinjection molding. The term "inert" in the context of the present invention means that the material does react neither with compound A and compound B contained in the system of the present invention nor with their reaction products that form after activation of the system of the present invention. The term "biocompatible" in the context of the present invention means that the material is suitable for pharmaceutical applications, particularly that the material is in accordance with DIN EN ISO 10993 (1 to 20) and/or USP Class VI.

The first unit is preferably made of a thermoplastic material. Thermoplastic materials are generally polymers that become pliable or moldable at elevated temperatures and solidify upon cooling. The thermoplastic materials for use in the present invention include polymers that can be processed by means of laser sintering or by injection molding. The thermoplastic materials for use in the present invention are furthermore biocompatible, which means that they are suitable for pharmaceutical applications, particularly that they are in accordance with DIN EN ISO 10993 and/or USP Class VI, as mentioned above. Such materials for example include polyamides, acrylic polymers, polylactic acids, polyethylene, and polytetrafluoroethylene. A preferred thermoplastic material for the first unit is polyamide.

The second unit is preferably made of a thermoset material (duroplast). Thermoset materials are generally polymers that are irreversibly hardened by curing of liquid or soft viscous pre-polymer material. In the context of the present invention, these duroplasts are biocompatible duroplasts, which means that they are suitable for pharmaceutical applications, particularly that they are in accordance with DIN EN ISO 10993 and/or USP Class VI, as mentioned above. Curing can e.g. be achieved by applying heat, a catalyst or ultraviolet light, resulting in a crosslinking reaction. Once the pre-polymer material has been cured, it cannot be softened again upon reheating. For the purpose of the present invention, the thermoset material is biocompatible and impermeable for water. Such materials include for example polyacrylate resins, epoxy resins, polyester resins, polyurethanes and cycloolefine polymers, which are impermeable for water so that compound B can be used in form of an aqueous solution in the system of the present invention. Preferred thermoset materials for the second unit are polyacrylate resins and epoxy resins. The top used to close the second unit is preferably made of the same material as the second unit.

The characteristics of the membrane, in particular the wall thickness and the shore hardness of the outer membrane, influence the release rate of the produced therapeutic gas. An outer membrane with a lower wall thickness and/or a shore hardness supports a fast release of the therapeutic gas, which is beneficial for the treatment of an early stage of the gastrointestinal tract, such as the stomach. An outer membrane with a higher wall thickness and/or shore hardness supports a slow release of the therapeutic gas from the system of the present invention, which is beneficial for treating later stages of the gastrointestinal tract, such as the small intestine and the colon.

For a system that releases the therapeutic gas over a shorter period of time, an outer membrane with a wall thickness of preferably between 0.3 and 0.9 mm, more preferably between 0.33 and 0.7 mm, even more preferably between 0.35 and 0.5 mm is used.

Such characteristics of the outer membrane typically provide release rates, wherein 90% of the maximum amount of the therapeutic gas is released within a time period of less than 240 min, preferably less than 180 min, more preferably less than 150 min, which is particularly suitable for therapy of tissue in an early stage of the gastrointestinal tract, such as the stomach area.

For a system that releases the therapeutic gas over an extended period of time, an outer membrane with a wall thickness of preferably between 0.9 and 2.0 mm, more preferably between 1.2 and 1.8 mm, even more preferably between 1.4 and 1.6 mm is used. Such characteristics of the outer membrane provide release rates, wherein 90% of the maximum amount of the therapeutic gas is released within a time period of more than 4 hours, preferably more than 8 hours, more preferably more than 12 hours, which is particularly suitable for therapy of tissue in later stages of the gastrointestinal tract, including the small intestine and the colon.

The outer membrane can have the following further characteristics:

outer diameter between 6 and 9 mm, preferably between 6.5 and 7.5 mm, more preferably between 6.4 and 6.8 mm, a tear strength of at least 8.0 MPa, an extension of break point of at least 500%, and a shore hardness A between 50 and 100.

Typically, the size of the system of the present invention corresponds to the usual standard sizes for drug capsules (i.e. size 000 to size 4), which allows that the system of the present invention can be easily swallowed by the patient and is excreted without remaining in or even clogging the gastrointestinal tract. A typical size for the system of the present invention is e.g. 18-22 mm×6-8 mm. The system of the present invention thus forms a unit (which can e.g. also be designated as a capsule) suitable for oral administration.

Therapeutic gas releasing compounds A and therapeutic gas release triggering compounds B that are suitable for use in the present invention have been described in WO 2015/188941 A1, WO 2016/110517 A1 and DE 10 2017 006 393 A1. Preferably, the therapeutic gas releasing compound for use in the present invention is a carbon monoxide (CO), hydrogen sulfide ($H_2S$) or nitric oxide (NO) releasing molecule. In one embodiment, the therapeutic gas releasing compound is a metal organic compound.

Preferred as the therapeutic gas releasing compound A is a carbon monoxide releasing molecule (CORM), resulting in release of carbon monoxide (CO) as the therapeutic gas.

Preferably, the carbon monoxide releasing molecule (CORM) is a metal carbonyl compound. The metal carbonyl compound comprises e.g. a complex of an element of the group of Rh, Ti, Os, Cr, Mn, Fe, Co, Mo, Ru, W, Re, Ir, B and C. More preferably, the metal carbonyl compound comprises a complex of an element of the group of Rh, Mo, Mn, Fe, Ru, B and C, even more preferably of the group of Rh, Fe, Mn, Mo, B and C. The metal carbonyl compounds may be regarded as complexes, because they comprise CO groups coordinated to a metal center. However, the metal may be bonded to other groups by other than coordination bonds, e.g. by ionic or covalent bonds. Thus, groups other than CO, which form part of the metal carbonyl compound, need not strictly be "ligands" in the sense of being coordinated to a metal center via a lone electron pair, but are referred to herein as "ligands" for ease of reference.

Thus, the ligands to the metal may all be carbonyl ligands. Alternatively, the carbonyl compound may comprise at least one ligand which is not CO. Ligands which are not CO are typically neutral or anionic ligands, such as halide, or derived from Lewis bases and having N, P, O or S or a conjugated carbon group as the coordinating atom(s). Preferred coordinating atoms are N, O and S. Examples include, but are not limited to, sulfoxides such as dimethylsulfoxide, natural and synthetic amino acids and their salts for example, glycine, cysteine, and proline, amines such as $NEt_3$ and $H_2NCH_2CH_2NH_2$, aromatic bases and their analogues, for example, bi-2,2'-pyridyl, indole, pyrimidine and cytidine, pyrroles such as biliverdin and bilirubin, drug molecules such as YC-1 (2-(5'-hydroxymethyl-2'-furyl)-1-benzylindazole), thiols and thiolates such as EtSH and PhSH, chloride, bromide and iodide, carboxylates such as formate, acetate, and oxalate, ethers such as Et 2 O and tetrahydrofuran, alcohols such as EtOH, and nitriles such as MeCN. Other possible ligands are conjugated carbon groups, such as dienes, e.g. cyclopentadiene ($C_5H_5$) or substituted cyclopentadiene. The substituent group in substituted cyclopentadiene may be for example an alkanol, an ether or an ester, e.g. $-(CH_2)_nOH$ where n is 1 to 4, particularly $-CH_2OH$, $-(CH_2)_nOR$ where n is 1 to 4 and R is hydrocarbon preferably alkyl of 1 to 4 carbon atoms and $-(CH_2)_nOOCR$ where n is 1 to 4 and R is hydrocarbon preferably alkyl of 1 to 4 carbon atoms. The preferred metal in such a cyclopentadiene or substituted cyclopentadiene carbonyl complex is Fe.

It is also explicitly referred to WO 2008/130261 and US 2007/0219120 A1 for a description of carbon monoxide releasing compounds. There aldehydes according to formula I formula I

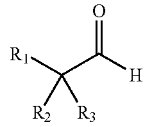

are disclosed which can also be used as therapeutic gas release compound A in the present invention wherein $R_1$, $R_2$ and $R_3$ are each independently selected from alkyl, substituted alkyl, cycloalkyl, substituted cycloalkyl, heterocyclyl, substituted heterocyclyl, alkylheterocyclyl, substituted alkylheterocyclyl, alkenyl, substituted alkenyl, aryl, substituted aryl, heteroaryl, substituted heteroaryl, alkylaryl, substituted alkylaryl, wherein the number of C atoms is 1-12 or 1-6 in each case hydroxy, alkoxy, amino, alkylamino, mercapto, alkylmercapto, aryloxy, substituted aryloxy, heteroaryloxy, substituted heteroaryloxy, alkoxycarbonyl, acyl, acyloxy, acylamino, alkylsulfonyl, alkylsulfinyl, F, Cl, Br, $NO_2$ and cyano; or two or more of $R_1$, $R_2$ and $R_3$ are taken together to form a substituted or unsubstituted carbocyclic or heterocyclic ring structure or an derivative thereof. For any substituent the number of C atoms is 1-12 or 1-6.

A derivative of a compound of formula I being an acetal, hemiacetal, aminocarbinol, aminal, imine, enaminone, imidate, amidine, iminium salt, sodium bissulfite adduct, hemimercaptal, dithioacetal, 1,3-dioxepane, 1,3-dioxane, 1,3-dioxalane, 1,3-dioxetane, α-hydroxy-1,3-dioxepane, α-hydroxy-1,3-dioxane, α-hydroxy-1,3-dioxalane, α-keto-1,3-dioxepane, α-keto-1,3-dioxane, α-keto-1,3-dioxalane, α-keto-1,3-dioxetane, macrocyclic ester/imine, macrocyclic ester/hemiacetal, oxazolidine, tetrahydro-1,3-oxazine, oxazolidinone, tetrahydro-oxazinone, 1,3,4-oxadiazine, thiazolidine, tetrahydro-1,3-thiazine, thiazolidinone, tetrahydro-1,3-thiazinone, imidazolidine, hexahydro-1,3-pyrimidine, imidazolidinone, tetrahydro-1,3-pyrimidinone, oxime, hydrazone, carbazone, thiocarbazone, semicarbazone, semithiocarbazone, acyloxyalkyl ester derivative, O-acyloxyalkyl derivative, N-acyloxyalkyl derivative, N-Mannich base derivative or N-hydroxymethyl derivative can also be used as carbon monoxide release compound A in the present invention.

The carbon monoxide releasing compound of the present invention can e.g. also be trimethylacetaldehyde, 2,2-dimethyl-4-pentenal, 4-ethyl-4-formyl-hexanenitrile, 3-hydroxy-2,2-dimethylpropanal, 2-formyl-2-methyl-propylmethanoate, 2-ethyl-2-methyl-propionaldehyde, 2,2-dimethyl-3-(p-methylphenyl)propanal or 2-methyl-2-phenylpropionaldehyde.

In one embodiment, an oxalate, an oxalate ester or amide is used as carbon monoxide release compound A comprised in the device of the present invention.

Preferred carbon monoxide releasing compounds for use in the present invention include molybdenum carbonyl compounds, CORM-1, CORM-2, CORM-3, CORM-401, as e.g. disclosed in WO 2015/188941 A1, WO 2016/110517 A1 and DE 10 2017 006 393 A1.

More preferred are molybdenum-based CORMs, such as $Mo(CO)_3(CNC(CH_3)_2COOH)_3$ (also designated as "CORM-ALF794") and $Mo(CO)_3(CNCH_2CO_2H)_3$ (Tricarbonyl[tris(isocyanoaceticacid)]molybdenum(0), also designated herein as "Beck-1"), wherein $Mo(CO)_3(CNCH_2CO_2H)_3$ is particularly preferred. Preferably, $Mo(CO)_3(CNCH_2CO_2H)_3$ is then used as the tri-sodium salt $(Mo(CO)_3(CNCH_2CO_2Na)_3)$.

In one embodiment of the present invention, a metal organic framework loaded with a therapeutic gas is used as therapeutic gas release compound A. Metal-organic frameworks (MOFs) are coordination polymers with an inorganic-organic hybrid frame comprising metal ions and organic ligands coordinated with the metal ions. In one embodiment, the therapeutic gas release compound A is a MOF loaded with at least one Lewis base gas chosen from the group comprising of NO, CO and $H_2S$, such as MIL-88B-FE or $NH_2$-MIL-88B-Fe. In another embodiment the therapeutic gas release compound A comprised in the device of the present invention is a MOF loaded with at least one Lewis base gas chosen from the group comprising NO, CO and $H_2S$ as described in WO 2009/133278 A1, particularly as described in items 1 to 13 therein to which it is explicitly referred.

As hydrogen sulfide ($H_2S$) releasing compound, a sulfide, disulfide or a polysulfide can e.g. be used. For example, NaSH and $Na_2S$ are $H_2S$ releasing molecules particularly usable in the present invention. GYY 4137 (CAS 106740-09-4) is another $H_2S$ releasing molecule usable in the present invention.

Nitric oxide (NO) releasing compounds include e.g. diazeniumdiolates. Non-diazeniumdiolate forms of NO donors including S-nitroso compounds and C-nitroso compounds may also be used. NO-releasing imidates, thioimidates, methanetrisdiazeniumdiolate, and a bisdiazeniumdiolate derived from 1,4-benzoquinone dioxime can e.g. also be used.

Therapeutic gas release triggering compounds suitable for use in the present invention have been described in WO 2015/188941 A1, WO 2016/110517 A1 and DE 10 2017 006 393 A1.

The therapeutic gas release compound A releases therapeutic gas upon contact with the therapeutic gas release triggering compound B ("trigger compound"). "Contact" means that a reaction between the therapeutic gas release compound A and the trigger compound can take place, which results in therapeutic gas release. Upon contact with the trigger compound B, the gas releasing compound A starts to release substantial amounts of gas. The system is then "activated", as explained above, and ready for oral administration.

The trigger compound B is preferably a sulfur-containing compound, a nitrogen-containing compound, an oxidizing compound, an acid or a base, or water.

When the therapeutic gas release compound A is a metal carbonyl compound, the trigger compound can e.g. be a carbonyl substituting agent, such a sulfur-containing compound or a nitrogen-containing compound. The sulfur-containing compound can e.g. be selected from an alkali metal or alkaline-earth metal salt, preferably a sodium salt of sulfite, dithionite, or metabisulfite, or a compound bearing at least one thiol moiety, such as cysteine or glutathione.

Examples of oxidizing compounds to be used as trigger compounds in the present invention include peroxides, perborates, percarbonates, and nitrates of which calciumperoxide, dibenzoylperoxide, hydrogen peroxide urea, sodium perborate, and sodium percarbonate are preferred. Oxidizing metal salts that can be used as trigger compounds include and silver(I)nitrate, iron(III)chloride, potassium permanganate, cer(IV)sulfate, potassium dichromate, gold(III)chloride and silver nitrate, wherein iron(III)chloride, potassium permanganate and cer(IV)sulfate and, in particular, iron(III) chloride and cer(IV)sulfate, are preferred. The oxidizing metal salts are preferably used in aqueous solution.

As acids, e.g. HCl can be used. In a further embodiment, the trigger compound is a non-enzymatic compound. Preferably, the trigger compound is a compound with a molecular weight of less than 10,000 g/mol, more preferably of less than 7,000 g/mol or even less than 1,000 g/mol. The trigger compound can, e.g., also be water or a solvent. A preferred therapeutic gas release compound A which releases gas upon contact with water is ALF186.

For a metal carbonyl compound as therapeutic gas release compound A and a sulfur-containing compound or other electron withdrawing compound as the trigger compound B, it is e.g. believed that, when this trigger compound comes into contact with the metal carbonyl compound, a ligand substitution takes place, thereby triggering gas release.

When the therapeutic gas release compound A is sodium sulfide, an acid such as HCl can e.g. be used as trigger compound to trigger gas release ($H_2S$) from the therapeutic gas release compound A (sodium sulfide).

When the therapeutic gas release compound A is an S-nitroso compound, a copper ion, such as copper (II) sulfate and copper (I) chloride can be used to trigger gas release (NO) from the therapeutic gas release compound A.

In another embodiment of the present invention, the trigger compound B is selected from the group consisting of a sulfur-containing compound, a nitrogen-containing compound, an oxidizing compound and water. This is in particular the case, when the therapeutic gas release compound A is a metal carbonyl compound.

In preferred embodiments, molybdenum carbonyl compounds are used as the therapeutic gas releasing compound A and oxidizing compounds are used as the therapeutic gas release triggering compound B. In a further preferred alternative preferred embodiment, CORM-2 ($Ru_2(CO)_6Cl_4$) is used as the therapeutic gas releasing compound A and sodium sulfite ($Na_2SO_3$) is used as the therapeutic gas release triggering compound B.

Particularly preferred embodiments include combinations of a molybdenum carbonyl compounds, preferably $Mo(CO)_3(CNCH_2COOH)_3$ (Beck-1) with iron(III)chloride ($FeCl_3$), cer(IV)sulfate ($Ce(SO_4)_2$) or $H_2O_2$, wherein $FeCl_3$ and $Ce(SO_4)_2$ are used as aqueous solutions at concentrations between 2 and 3 mol/L, and $H_2O_2$ is used as aqueous solution at a concentration of 30 wt.-% Molybdenum carbonyl compounds have the advantage of producing CO at a high capacity (95%) and with a high purity (>95%). For achieving a particularly high CO production with a particularly high purity, it is particularly preferred to use Beck 1 ($Mo(CO)_3(CNCH_2COOH)_3$) in combination with $FeCl_3$.

The therapeutic gas release system of the present invention releases a therapeutic gas in a therapeutically effective amount when administered to a patient. In a preferred embodiment, the therapeutic system of the present invention releases between 0.1 and 100 μmol of the therapeutic gas, preferably of carbon monoxide, when administered to a patient.

The amount of therapeutic gas to be released from the therapeutic gas release system of the present invention can be tailored, e.g. by the choice and amount of therapeutic gas release compound A and by the choice and amount of the trigger compound B.

Typical weight amounts for the therapeutic gas release compound A in the system of the present invention range from 1 mg to 200 mg, preferably 5 mg to 100 mg, more preferably 10 mg to 50 mg. Typical molar amounts for the therapeutic gas release compound A range from 5 μmol to 100 μmol, preferably 10 μmol to 60 μmol more preferably 20 μmol to 40 μmol.

The gas release triggering compound B is typically used in a 10-fold molar excess relative to the therapeutic gas release compound A, i.e. in a range from 50 to 800 μmol, preferably 100 μmol to 600 μmol, e.g. 300 μmol to 600 μmol or 200 μmol to 400 μmol.

Preferably, the therapeutic gas release triggering compound B is used in aqueous solution because the chemical reaction between compound A and compound B upon proceeds better in solution or in a suspension. Typical concentrations for the therapeutic gas release triggering compound B range from 0.5 mol/L to 10 mol/L, preferably 1 mol/L to 5 mol/L, more preferably 2 mol/L to 3 mol/L.

Figure 3:
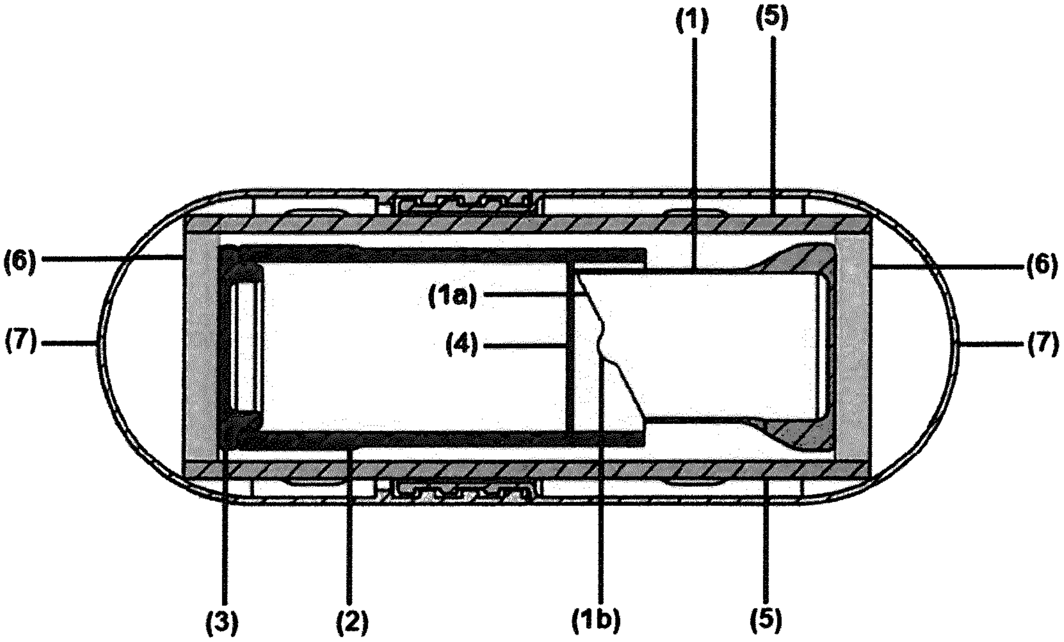
FIG. 3 is a cross-sectional view of a further preferred embodiment of the present invention, wherein (1) is the first unit comprising an obliquely tapered hollow tip opening (1a) with one or more elevations (1b) pointing towards the inner septum; (2) is the second unit; (3) is a top closing the open end of the second unit; (4) is the inner septum separating compound A and compound B from each other during storage of the system, wherein the inner septum is shifted towards the center of the second unit; (5) is a tubular outer membrane surrounding the first and second unit; (6) is an adhesive, preferably a silicone adhesive, closing the open ends of the outer membrane; and (7) is a protective shell surrounding the system of the present invention; wherein the system is configured that the first unit is pushed towards the inner septum by compressing the protective shell at the hemispherically shaped ends, causing the inner septum to break.

In order to provide additional protection against mechanical stress during transit through the gastrointestinal tract (which may be caused by the muscle movement in the gastrointestinal tract), the system of the present invention can be provided with a protective shell surrounding the system. A possible structure of the system of the present invention surrounded with a protective shell is shown in FIG. 3. The structure of the protective shell is designed that, by compressing the protective shell at the hemispherically shaped ends before oral administration, the obliquely tapered tip of the first unit breaks through the inner septum. This eliminates the need for activation and subsequent insertion of the activated capsule into the protective shell. The protective shell does not dissolve or disintegrate during transit through the gastrointestinal tract. Similar materials can be used as described for the first and second unit above, i.e. inert and biocompatible polymer materials, which can be produced by 3D printing (e.g. selective laser sintering or poly-jet modelling) or by microinjection molding. In order to allow therapeutic gas release in this embodiment, the protective shell contains openings.

The present invention allows local therapy of the gastrointestinal tract. The therapeutic gas released from the system of the present invention primarily interacts with local tissue, thereby bringing the therapeutic benefits directly to the infected region of the gastrointestinal tract.

This is particularly useful for the treatment of inflammatory diseases of the gastrointestinal tract, wherein said inflammatory diseases are preferably selected from the group consisting of colitis ulcerosa, gastric ulcera, postoperative ileus, diabetic gastropareses and Morbus Crohn, which are preferably treated with carbon monoxide as the therapeutic gas released from the system of the present invention.

The invention shall be illustrated in the following examples.

Example 1: CO Release Rates

This example illustrates the influence of the wall thickness of the silicone membrane on the release rate of the therapeutic gas.

TABLE 1

| Entry | CORM | Trigger | System | Wall thickness outer silicone membrane [mm] |
|---|---|---|---|---|
| 1 | Beck-1 (1 mg) | $FeCl_3$ | Free carbonyl | — |
| 2 | Beck-1 (15 mg) | $FeCl_3$ | OCORS | 0.4 |
| 3 | CORM-2 (50 mg) | $Na_2SO_3$ | OCORS | 1.5 |

| Entry | $C_{max}$ [ppm] | $T_{max}$ [min] | $C_{90\%}$[ppm] | $T_{90\%}$ [min] |
|---|---|---|---|---|
| 1 | 640.8 | 44 | 576.7 | 17 |
| 2 | 1133.4 | 259 | 1020.0 | 123 |
| 3 | 1130.6 | 1385 | 1017.6 | 936 |

OCORS = Oral carbon monoxide release system in accordance with the present invention The trigger compounds $FeCl_3$ and $Na_2SO_3$ were used in aqueous solution and in molar excess amounts relative to the CORM.

In Table 1, $C_{max}$ describes the highest value measured for the therapeutic gas concentration. $T_{max}$ is the time, at which this value was measured. 090% describes 90% of $C_{max}$, and $T_{90\%}$ is the time point, at which 90% of $C_{max}$ were released. For the free metal carbonyl, a different release vessel was used than for the CO releasing systems, and therefore, the absolute values for $C_{max}$ differ.

Figure 4:
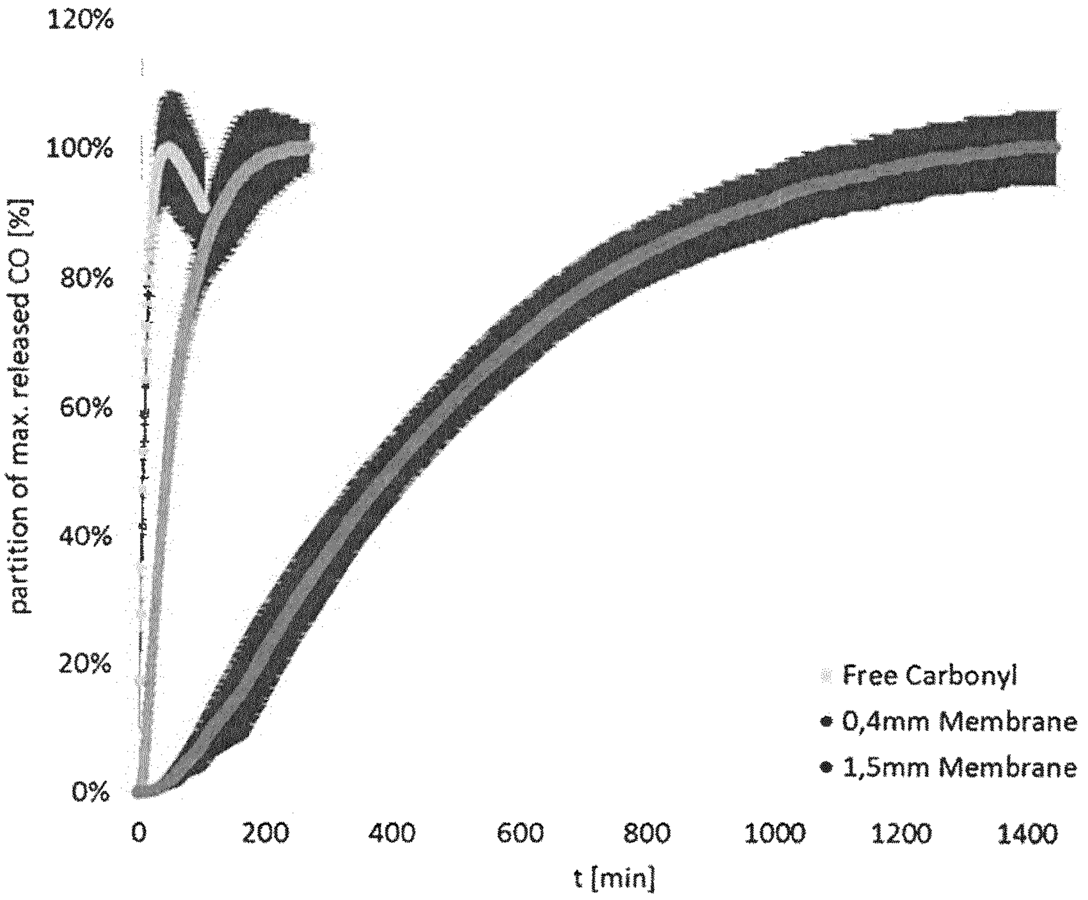
FIG. 4 shows the CO release rates for (i) a free metal carbonyl compound, (ii) a release system in accordance with the present invention with a wall thickness of the outer silicon membrane of 0.4 mm, and (iii) a release system in accordance with the present invention with a wall thickness of the outer silicon membrane of 1.5 mm.

FIG. 4 shows the release rates for CO from (i) the free CORM, (ii) a therapeutic gas release system in accordance with the present invention having a silicon membrane with a wall thickness of 0.4 mm, and (iii) a therapeutic gas release system in accordance with the present invention having a silicon membrane with a wall thickness of 1.5 mm.

As can be taken from Table 1 and FIG. 4, the release rate can be controlled by the wall thickness of the outer membrane. A thinner wall supports fast release, whereas a thicker wall allows slow release of the therapeutic gas.

Example 2: Determination of Breaking Force

For the determination of the breaking force required to break the inner septum in a therapeutic gas release system in accordance with the embodiment shown in FIG. 1, a Dr. Schleuniger® Pharmatron 8M Tablet Hardness Tester was used.

Figure 5:
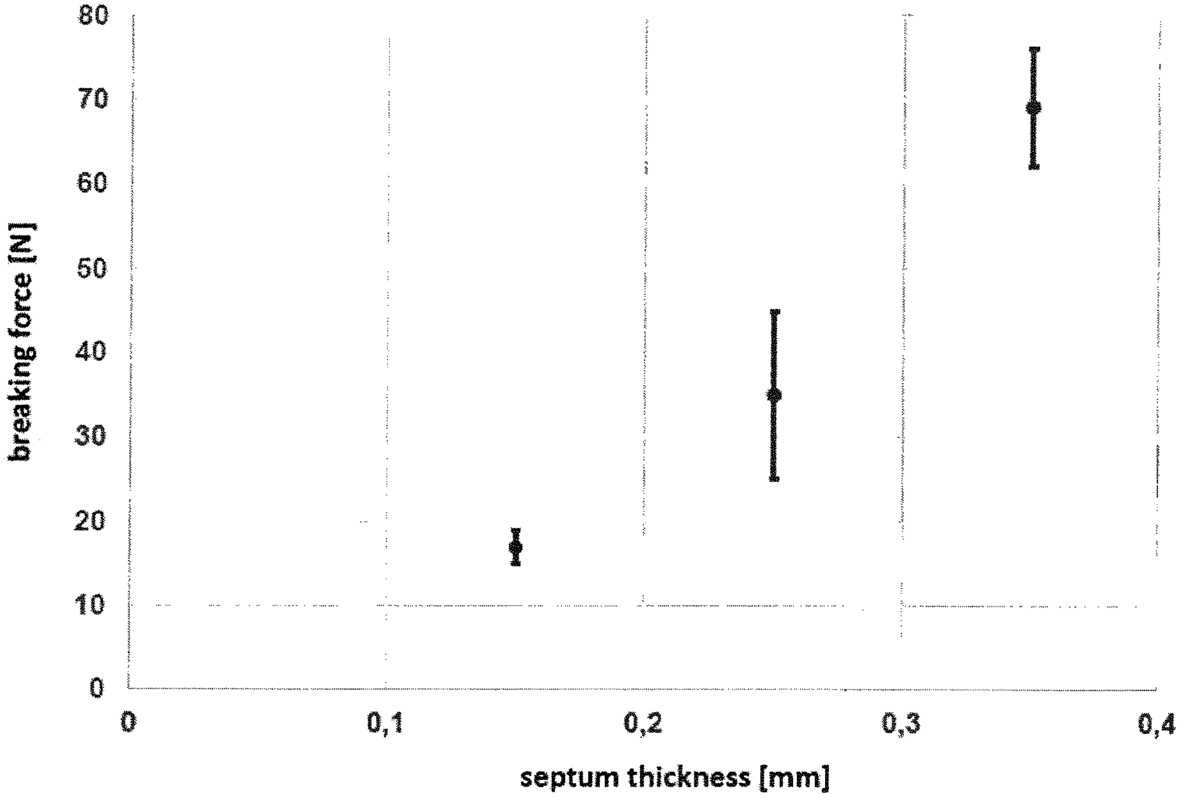
FIG. 5 illustrates the breaking force as a function of the thickness of the inner septum at a given material of the inner septum (Duroplast, Med610, Stratasys, Eden Prairie MN, USA).

FIG. 5 illustrates the breaking force as a function of the thickness of the inner septum at a given material of the inner septum (Duroplast, Med610, Stratasys, Eden Prairie MN, USA) in an embodiment as shown in FIG. 1. The data in FIG. 5 is presented as mean±SD, n=3.

Example 3: In Vivo Design Validation

A pig study was carried out, which aimed at design validation of an oral CO release system in accordance with the present invention in vivo. The endpoints of the study were:

a) Demonstration of CO release in vivo;
b) Demonstration of unit integrity during passage through the gastrointestinal tract of the animals;
c) Safety data on systemic safety (COHb formation).

For this purpose, the test animals were administered up to 3 units (capsules) of the oral CO release system in accordance with the embodiment shown in FIG. 1.

a) Demonstration of CO Release In Vivo

Figure 6:
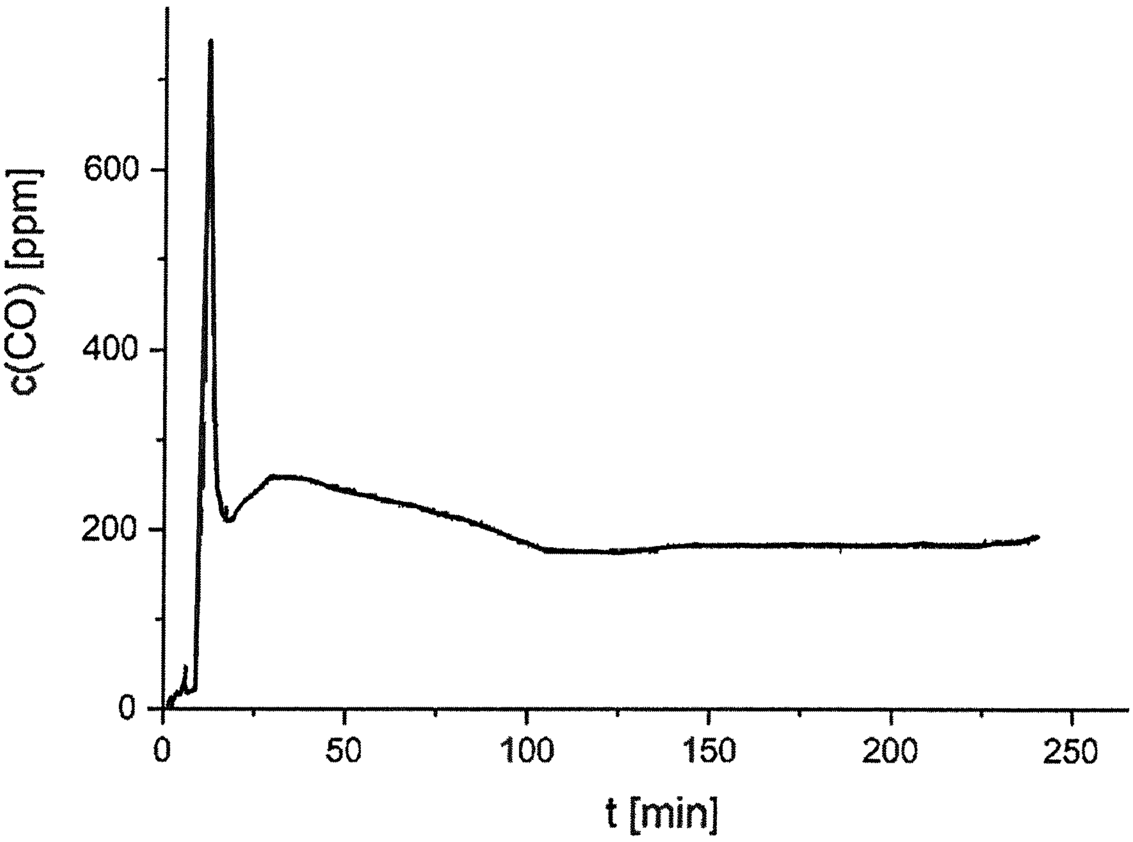
FIG. 6 illustrates CO release over 4 hours (240 min) from the system of the present invention in the stomach of an anesthetized pig.

This example attempts to demonstrate CO release of the oral CO release system in accordance with the present invention in the stomach of a pig FIG. 6 shows CO release over 4 hours (240 min) in the stomach of an anesthetized pig. The initial spike in the figure is a motion artefact of the gastric probe/sensor.

Hence, this example demonstrates that the system of the present invention releases CO in vivo and is accordingly suitable for its therapeutic purpose after oral administration.

b) System Integrity (Mechanical) integrity of the oral CO release system in accordance with the present invention after passage through the gastrointestinal tract of the pigs has been investigated by optical macroscopy in this example.

For this purpose, the animals were administered 3 capsules of the system of the present invention, which were to be recollected from the excrements of the animals after passage through the gastrointestinal tract. As can be taken from the following Table 2, all the recovered capsules successfully passed the test.

TABLE 2

| Animal code | Number of capsules recovered | Inspection passed? |
|---|---|---|
| 119.02 | 1 | Yes |
| 119.03 | 1 | Yes |
| 119.05 | 1 | Yes |
| | 2 | Yes |
| | 3 | Yes |
| 119.07 | 1 | Yes |
| | 2 | Yes |
| 119.08 | 1 | Yes |
| 119.13 | 1 | Yes |
| | 2 | Yes |

Hence, this example confirms that the system of the present invention maintains its structural integrity during transit through the gastrointestinal tract, which is important under safety aspects. The fact that not all capsules were recollected from all animals cannot be interpreted as a negative result in terms of mechanical integrity of the oral CO release system; it only means that these capsules were never found in the excrements of the animal or in the straw coverage of the floor of the animal housing area.

c) Systemic Safety (COHb Formation)

This example demonstrates systemic safety of the oral CO release system in accordance with the present invention in terms of formation of carboxyhemoglobin (COHb) by frequent monitoring of COHb values in the blood of the animals over a period of 5 days.

Figure 7:
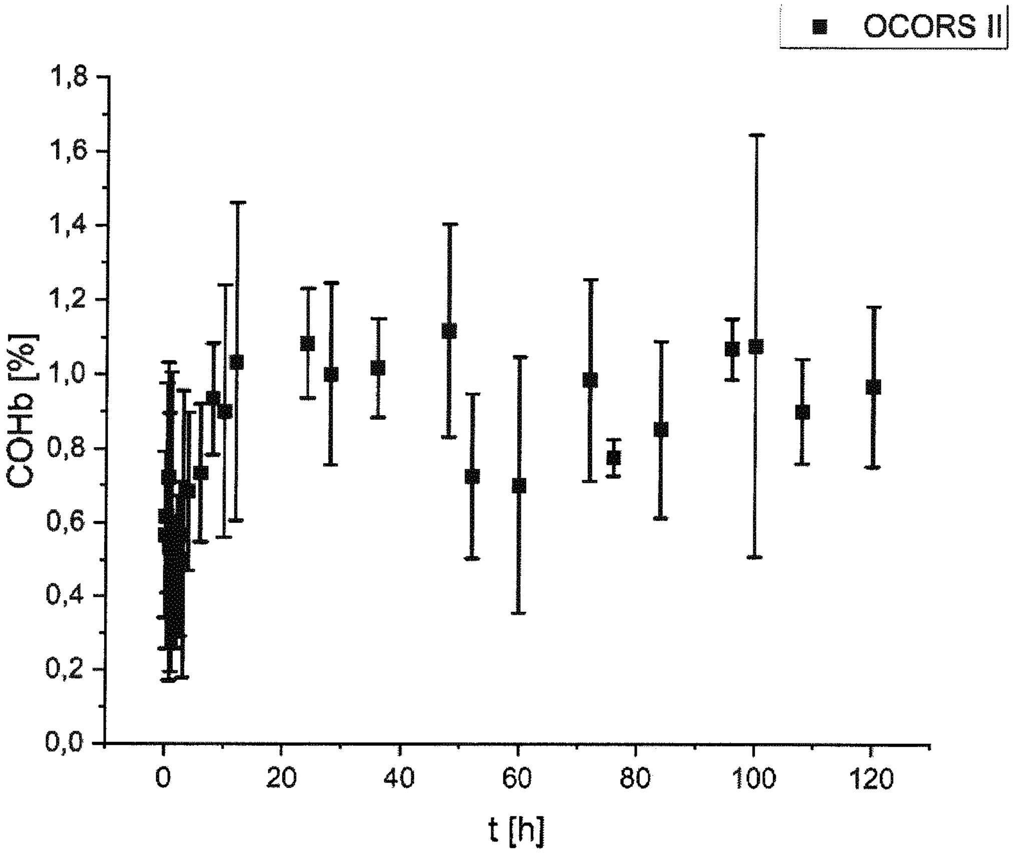
FIG. 7 shows COHb values in the blood of pigs after administration of 3 units (capsules) of an oral CO release system ("OCORS II") according to the present invention.

FIG. 7 shows COHb values in the blood of the animals after administration of 3 capsules of the oral CO release system ("OCORS II") according to the present invention, corresponding to 270 μmol of CO (data are presented as mean±SD, n=6).

All values shown in FIG. 7 are within the physiologically normal range during the observation period. The low start in the first 4 hours is due to exposure to >95% $FiO_2$ during anesthesia which increased the initial oxygen saturation of the animals.

The invention claimed is:

1. A therapeutic gas release system for oral administration comprising:

a therapeutic gas releasing compound A, and a therapeutic gas release triggering compound B, wherein compound A and compound B are separated from each other during storage of the system by an inner septum, wherein compound A is in a first unit and compound B is in a second unit, whereby the first and second units are surrounded by an outer membrane that is a gas-permeable and water- and solid-impermeable membrane, further wherein the inner septum forms part of the second unit and the first unit has an obliquely tapered, hollow tipped open end that pints towards the inner septum, further wherein therapeutic gas release from the system can be activated before oral administration by squeezing the system along a longitudinal axis, which in turn pushes the obliquely tapered, hollow tipped open end of first unit towards the inner septum, thereby causing the inner septum to break.

2. The therapeutic gas release system according to claim 1, wherein the inner septum breaks upon squeezing the system manually or in a partly automated process using an external activator device.

3. The therapeutic gas release system according to claim 1, wherein the second unit comprises a top that closes an open end of the second unit, further wherein the top is optionally glued to the second unit using an adhesive.

4. The therapeutic gas release system according to claim 1, wherein the first unit, the second unit and the top of the second unit are made of a biocompatible material.

5. The therapeutic gas release system according to claim 1, wherein the first unit is made of a thermoplastic material, and/or the second unit and/or the top of the second unit is/are made of a thermoset material.

6. The therapeutic gas release system according to claim 1, wherein the outer membrane is tubular, and wherein the open ends of the tubular outer membrane are closed with an adhesive.

7. The therapeutic gas release system according to claim 1, wherein the obliquely tapered, hollow tipped open end of the first unit includes one or more elevations that point towards the inner septum and facilitate its breakage.

8. The therapeutic gas release system according to claim 1, wherein the therapeutic gas is selected from the group consisting of carbon monoxide (CO), hydrogen sulfide ($H_2S$) and nitric oxide (NO).

9. The therapeutic gas release system according to claim 1, wherein compound A is selected from the group consisting of a carbon monoxide releasing molecule (CORM), a hydrogen sulfide ($H_2S$) releasing molecule and a nitric oxide (NO) releasing molecule.

10. The therapeutic gas release system according to claim 1, wherein compound B is selected from the group consisting of a sulfur containing compound, a nitrogen containing compound, an oxidizing compound and water.

11. The therapeutic gas release system according to claim 1, wherein the therapeutic gas is carbon monoxide (CO), the therapeutic gas releasing compound A is a molybdenum carbonyl compound, and the therapeutic gas release triggering compound B is selected from the group consisting of $FeCl_3$, $Ce(SO_4)_2$ and $H_2O_2$.

12. The therapeutic gas release system according to claim 1, wherein the system is surrounded by a protective shell.

13. The therapeutic gas release system according to claim 1, wherein the gas-permeable and water- and solid-impermeable outer membrane is a silicone membrane.

14. The therapeutic gas release system according to claim 5, wherein the thermoplastic material is a polyamide and the thermoset material is an acrylic resin or an epoxy resin.

15. The therapeutic gas release system according to claim 8, wherein the therapeutic gas is carbon monoxide (CO).

16. The therapeutic gas release system according to claim 8, wherein the therapeutic gas releasing compound A is a carbon monoxide releasing molecule.

17. The therapeutic gas release system according to claim 16, wherein the carbon monoxide releasing molecule is a metal carbonyl compound.

18. The therapeutic gas release system according to claim 11, wherein the molybdenum carbonyl compound is $Mo(CO)_3(CNCH_2CO_2H)_3$, and the therapeutic gas release triggering compound B is $FeCl_3$.

* * * * *